United States Patent
Otsubo

(10) Patent No.: US 7,524,314 B2
(45) Date of Patent: Apr. 28, 2009

(54) WEARING ARTICLE HAVING WAIST FASTENING ELEMENTS WITH INSERTS AND POCKETS

(75) Inventor: Toshifumi Otsubo, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 330 days.

(21) Appl. No.: 11/091,593

(22) Filed: Mar. 29, 2005

(65) Prior Publication Data

US 2005/0222551 A1    Oct. 6, 2005

(30) Foreign Application Priority Data

Mar. 31, 2004    (JP)    ............... 2004-107940

(51) Int. Cl.
A61F 13/15    (2006.01)
A61F 13/20    (2006.01)
A41B 9/00    (2006.01)
(52) U.S. Cl. .................. 604/391; 2/78.4; 604/386
(58) Field of Classification Search .............. 2/78.4; 24/442–448; 604/389–391, 385.01
See application file for complete search history.

(56) References Cited

U.S. PATENT DOCUMENTS 2,717,437 A * 9/1955 de Mestral ............ 428/92
3,503,101 A * 3/1970 Kolozsvary ............ 24/443
4,787,897 A * 11/1988 Torimae et al. ........... 604/389
4,850,990 A 7/1989 Huntoon et al.
5,235,515 A * 8/1993 Ungpiyakul et al. ........ 700/125
5,899,895 A * 5/1999 Robles et al. .......... 604/385.29
6,210,390 B1 * 4/2001 Karlsson ................ 604/391
6,746,976 B1 * 6/2004 Urankar et al. .......... 442/155
2003/0100880 A1 * 5/2003 Magee et al. ............ 604/389

FOREIGN PATENT DOCUMENTS

EP        0324578 A1 *  1/1989
WO        WO 00/01339     1/2000
WO        WO 00/01339 A1 *  1/2000
WO        WO 02/11657     2/2002
WO        WO 02/051278    7/2002
WO        WO 02051278 A2 *  7/2002

OTHER PUBLICATIONS

Zola, Annotated Drawings from EP 0324578A1, Jan. 1989, all figures.*
Martin, Annotated Drawings from WO 02/051278A2, Jul. 2002, figure 2.*

* cited by examiner

*Primary Examiner*—Tatyana Zalukaeva
*Assistant Examiner*—Melanie J Hand
(74) *Attorney, Agent, or Firm*—Lowe Hauptman Ham & Berner, LLP

(57) ABSTRACT

The wearing article is provided with a fastening system adapted to releasably connecting front and rear waist regions defining a waist-opening. The fastening system includes engaging fasteners located on transversely opposite side edges of the rear waist region and landing fasteners located on transversely opposite side zones of the front waist region. Each of the engaging fasteners has an insert and an engaging portion while each of the landing fasteners has a pocket adapted to receive the insert and a landing portion which is formed on the outer surface of the pocket and with which the engaging portion is releasably engaged.

18 Claims, 3 Drawing Sheets

WEARING ARTICLE HAVING WAIST FASTENING ELEMENTS WITH INSERTS AND POCKETS

RELATED APPLICATIONS

The present application is based on, and claims priority from, Japanese Application Number 2004-107940, filed Mar. 31, 2004, the disclosure of which is hereby incorporated by reference herein in its entirety.

BACKGROUND OF THE INVENTION

The present invention relates to wearing articles for direct and indirect containment of body wastes and having so-called waist fasteners. More particularly, the present invention relates to such wearing articles provided with a fixed point type fastening system used to fasten a waist region of the wearing article, particularly, such as disposable diapers, diaper covers, training pants, incontinence pants or the like and thereby to retain the article about an appropriate region of a wearer's body.

A fixed point type fastening system is well known (See WO 02/051278 A2, hereinafter referred to as "Citation 1"). The fastening system disclosed in Citation 1 comprises a first component having a hollow portion and a second component adapted to be inserted into this hollow portion. The hollow portion at least partially defines a surface adapted to be releasably engaged with at least one surface defined by the second component. These two surfaces adapted to be releasably engaged with each other respectively comprise a plurality of hooks and a plurality of loops. It is claimed by Citation 1 that such a fastener is advantageous for use with the absorbent article.

The absorbent article provided with an improved fastening system is also well known (See WO 02/11657 A2, hereinafter referred to as "Citation 2"). The fastening system disclosed in Citation 2 comprises face-to-face paired flap-like backings extending outward from each side edge in one of waist regions, on one hand, and a flap-like backing extending outward from each side edge in the other waist region and adapted to be interposed between the face-to-face paired flap-like backings, on the other hand. The face-to-face paired flap-like backings in the one waist region are provided on the inner surface thereof with a plurality of hooks and/or loops while the flap-like backing in the other waist region is provided on both the surfaces thereof with a plurality of loops and/or hooks adapted to be releasably engaged with the hooks and/or loops of the face-to-face paired flap-like backings.

In the case of the fastening system disclosed in Citation 1, basically characterized in that the second component is inserted into the hollow portion of the first component, both the hollow portion of the first component and the second component are provided with the hooks or the loops. These hooks and loops may be at least partially engaged one with another during insertion in the vicinity of entrance of the hollow portion and prevent the second component from being sufficiently inserted into the hollow portion. To solve such a problem, the user must insert the second component into the hollow portion with one hand while the hollow portion is sufficiently opened with the other hand. This fastening system is thus accompanied with inconvenience that the user must handle the fastening system with both hands in preparation for the wearing article.

The fastening system disclosed in Citation 2 also is accompanied with the inconvenience that the user fastening system must handle the fastening system with both hands in preparation for wearing the article. Specifically, the user must open the face-to-face paired flap on each side of the one waist region with both hands or one hand and then interpose the flap on each side of the other waist region between the face-to-face paired flaps with the other hand. In addition, this fastening system is disadvantageously distinguished from the fixed point type fastening system in that a position at which the hooks are engaged with the loops must be appropriately selected by the user him- or herself. So far as this aspect is concerned, the fastening system disclosed in Citation 2 is similar to the other fastening systems of prior art requiring such positioning.

It is assumed that the second component has not been properly inserted into the hollow portion of the first component as the fastening system disclosed in Citation 1 has often been the case or the positioning has not been properly selected as the fastening system disclosed in Citation 2 has often been the case. In both cases, it will be impossible to fasten the wearing article on the appropriate region of the wearer's body and consequentially the wearing article will readily slip down. Due to this, body wastes will leak beyond the leg-openings of the article.

SUMMARY OF THE INVENTION

It is an object of the present invention to provide a wearing article provided with a fixed point type fastening system allowing the user to carry out handling of the fastening system with one hand to fasten the article's front and rear waist regions together in such a manner that a possibility of body wastes leakage due to slip down of the article can be substantially eliminated.

According to the present invention, there is provided a wearing article comprising first and second waist regions each having body-facing surface and garment-facing surface, the first and second waist regions cooperating together to define a waist-opening, a crotch region extending between and cooperating with the first and second waist regions to define a pair of leg-openings, and a fastening system releasably connecting the first and second waist regions.

The fastening system according to the present invention comprises engaging fasteners respectively located on transversely opposite side edges of the first waist region and landing fasteners located on the garment-opposing surface of transversely opposite side zones of the second waist region. Each of the engaging fasteners has an insert and an engaging portion while each of the landing fasteners has a pocket adapted to receive the insert and a landing portion formed on an outer surface of the pocket so that the engaging portion releasably engages the landing portion.

At least one of the first and second waist regions is provided with a elastic means serving to elastically adjust a circumferential waist dimension defined by the first and second waist regions.

The present invention may include preferred embodiments as follow:

The engaging fasteners and the landing fasteners may be located along an elastically stretch- and contractable line created by the elastic means on the first and second waist regions.

The engaging portions and the inserts may include a rigid panel formed integrally therewith and the inserts slant at a given angle with respect to the engaging portions, respectively.

Each of the engaging portions may be formed by securing a hook member having a plurality of hook elements projecting from a sheet-like backing to a zone of the rigid panel defining the backing for the engaging portion.

Each of the engaging portions may be formed by coating a zone of the rigid panel defining the backing for the engaging portion with a pressure-sensitive adhesive.

Each of the pockets may be formed by a sleeve having an opening oriented outward with respect to a side edge of the second waist region to which this pocket is contiguous.

Each of the landing portions may be formed from a fibrous texture defining the sleeve and functioning as the loop elements.

Each of the landing portions may be formed by securing a loop member having a plurality of loop elements projecting from a sheet-like backing to the sleeve.

Each of the inserts may have a stiffness value in a range of 0.05N/cm to 2N/cm as measured by the Taber's method.

The elastic means may comprise a pair of elastically stretch- and contractable ear flaps extending outward from the side edges of the first waist region.

The first and second waist regions and the crotch region may be formed by an absorbent chassis.

The chassis may comprise a liquid-pervious inner sheet, a liquid-impervious outer sheet and a liquid-absorbent core interposed between these inner and outer sheets.

The wearing article according to the present invention may include a waist fastening mechanism in the form of a fixed point type fastening system composed of the engaging fasteners and the landing fasteners. For such a fixed point type fastening system, it is unnecessary to adjust the position at which the desired engagement should be established since the position of engagement is predetermined. Additionally, the wearer or his or her helper (e.g., mother, care-giver, etc.) may introduce the inserts of the respective engaging fasteners into the pockets of the respective landing fasteners through the respective openings with one hand and then press the engaging portions of the respective engaging fasteners against the landing portions of the respective landing fasteners to achieve the desired engagement between the engaging fasteners and the landing fasteners. For example, when the user wears the article while standing, it is unnecessary for the user to align relative positions of the engaging fasteners and the landing fasteners with both hands and to carefully bring these relative positions into engagement using both hands as it is necessary for the wearer lying down.

Once the engaging fasteners have been engaged with the landing fasteners in this manner, a circumferential waist dimension defined by the first and second waist regions is automatically adjusted under the elastic effect of the elastic means provided in at least one of the first and second waist regions. Such an automatic adjustment combined with the simplified operation for the engagement facilitates the wearer him- or her helper or the caregiver to put the article on the wearer's body.

The fixed point type fastening system ensures that the engaging fasteners engage the landing fasteners at appropriate positions and thereby the article is appropriately stabilized about the wearer's body. Thus, it is unlikely that an undesirable clearance might be created between the leg-openings of the article and the wearer's legs due to slip down of the article and consequentially body wastes might leak through such a clearance.

The embodiment of the invention wherein the engaging fasteners and the landing fasteners may be located along an elastically stretch- and contractable line created by the elastic means on the first and second waist regions allows a circumferential waist dimension defined by the first and second waist regions to be automatically and appropriately adjusted and allows the elastic means for this purpose to be effectively utilized.

According to the embodiment wherein the engaging portions and the inserts include a rigid panel formed integrally therewith and the inserts slant at a given angle with respect to the engaging portions, respectively as well as according to the embodiment wherein each of the pockets is formed by a sleeve having an opening oriented outward with respect to a side edge of the second waist region to which this pocket is contiguous, the engaging portions can be utilized as finger-grip tabs to introduce the inserts into the respective pockets quickly and reliably when the engaging fasteners are engaged with the landing fasteners. In addition, there is no anxiety that the article might slip down along the wearer's body because the rigid panel functions as a deformation-resistant, stabilizing support for the article against the movement of the wearer.

The embodiment of the invention wherein each of the engaging portions may be formed by securing a hook member having a plurality of hook elements projecting from a sheet-like backing to a zone of the rigid panel defining the backing for the engaging portion allows the hook member to be selected from those well known in the art. In addition, this embodiment allows the zone of the panel serving as the backing for the engaging portion to have a relatively low stiffness since the hook member has a relatively high stiffness.

The embodiment of the invention wherein each of the engaging portions may be formed by coating a zone of the rigid panel defining the backing for the engaging portion with a pressure-sensitive adhesive allows the engaging portion to be formed at a low cost merely by coating the predetermined zone with a pressure-sensitive adhesive.

The embodiment of the invention wherein each of the landing portions may be formed from a fibrous texture defining the sleeve and functioning as the loop elements allows the landing portion to be formed at a low cost without using a relatively expensive loop member.

The embodiment of the invention wherein each of the landing portions may be formed by securing a loop member having a plurality of loop elements projecting from a sheet-like backing to the sleeve allows the pocket to be formed from a material selected from a wide range of materials so far as the pocket can be formed by the selected material.

The embodiment of the invention wherein each of the inserts may have a stiffness value in a range of 0.05N/cm to 2N/cm as measured by the Taber's method facilitates it to introduce the insert into the pocket and eliminates an apprehension that the wearer might feel any discomfort due to the stiffness of the insert when the article is worn.

The embodiment of the invention wherein the elastic means may comprise a pair of elastically stretch- and contractible ear flaps extending outward from the side edges of the first waist region facilitate it to provide means automatically adjust a circumferential waist dimension defined by the first and second waist regions at a reduced cost.

The embodiment of the invention wherein the first and second waist regions as well as the crotch region may be formed by an absorbent chassis comprising, in turn, a liquid-pervious inner sheet, a liquid-impervious outer sheet and a liquid-absorbent core interposed between these inner and outer sheets makes it possible to provide the article being well capable of absorption and containment.

DETAILED DESCRIPTION OF THE PREFERRED EMBODIMENTS

Figure 1:
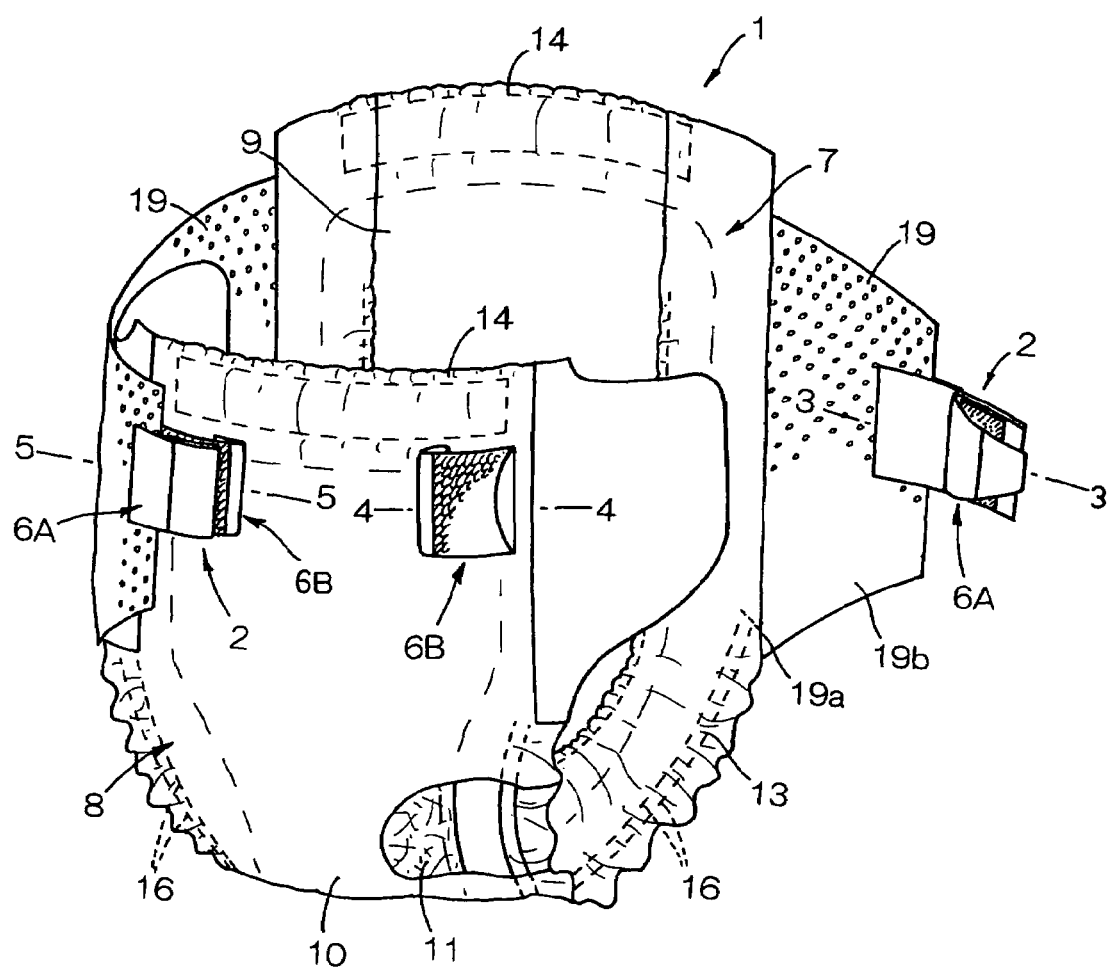
FIG. 1 is a partially cutaway perspective view showing a disposable diaper with front and rear waist regions opened along one of laterally opposite side edges and remaining closed along the other side edge.
Figure 2:
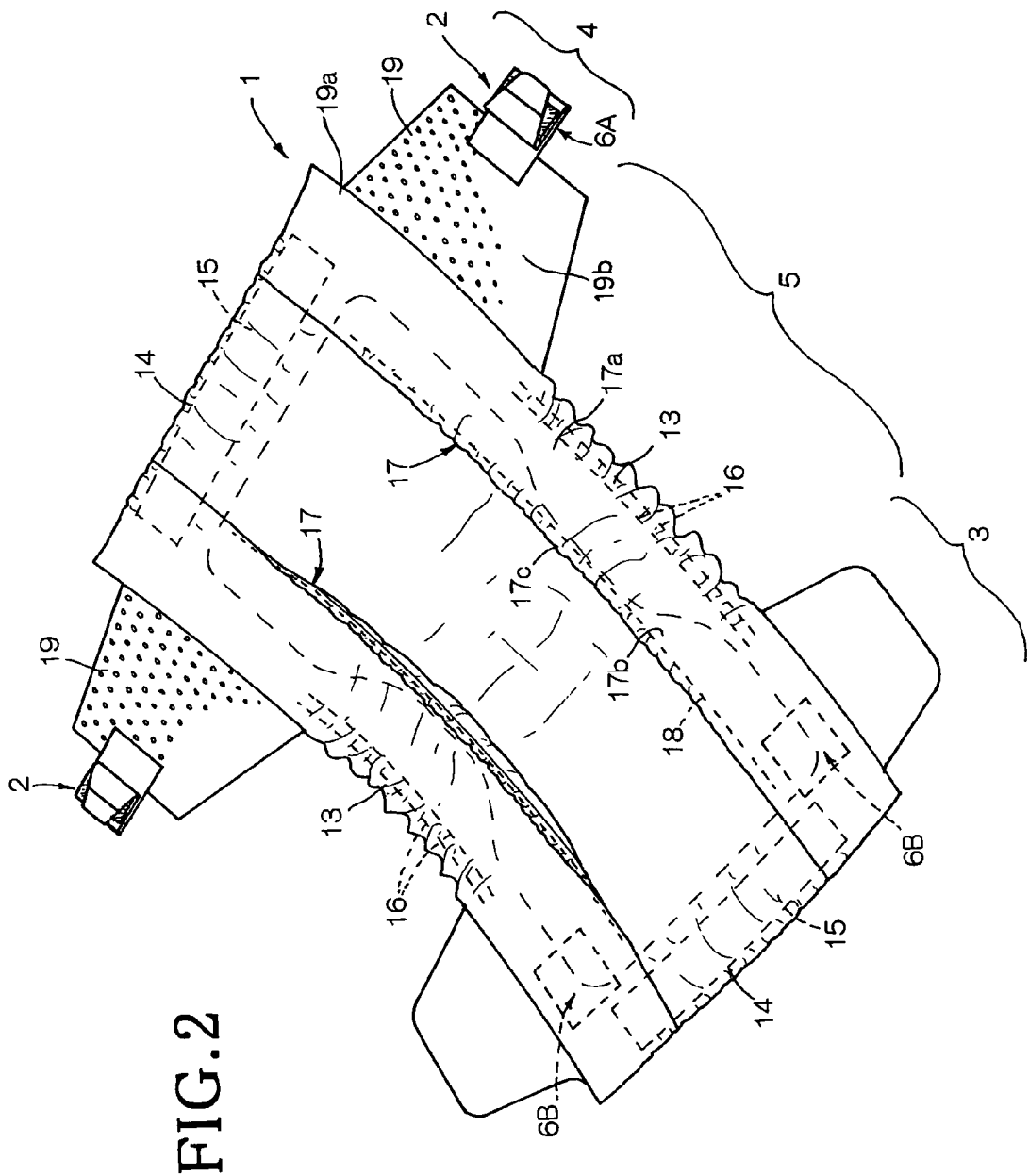
FIG. 2 is a perspective view showing said diaper developed with its inner surface opposed to the viewer.

FIGS. 1 and 2 show an open-type disposable diaper as a specific embodiment of the invention. The diaper includes an absorbent chassis 1 and a fastening means 2. The chassis 1 has a front waist region 3, a rear waist region 4 and a crotch region 5 extending between these waist regions 3, 4. The fastening means 2 comprise a pair of engaging fasteners 6A respectively attached to laterally opposite side edges of the rear waist region 4 and a pair of landing fasteners 6B respectively attached to laterally opposite side zones of the front waist region 3 on its surface facing the wearer's garment. The chassis 1 may be assembled by anchoring the engaging fasteners 6A onto the landing fasteners 6B and thereupon a waist-opening 7 and a pair of leg-openings 8 are defined.

The chassis 1 comprises a liquid-pervious inner sheet 9, a liquid-impervious outer sheet 10, a liquid-absorbent core 11 interposed and joined between these two sheets 9, 10 preferably by means of hot melt adhesives (not shown) intermittently applied thereto, and a pair of stretchable ear flaps 19 extending outward from the respective side edges of the rear waist region 4. The inner and outer sheets 9, 10 respectively include side and end flaps 13, 14 extending outward beyond a peripheral edge of the core 11.

The chassis 1 is provided with tape-like elastic members 15 attached thereto contractibly along the end flaps 14 which define the waist-opening 7 and with a plurality of strand-like elastic members 16 attached thereto contractibly along outer sides of the respective side flaps 13 which define the leg-openings 8. These elastic members are secured in a stretched state thereof within the side flaps 13 and the end flaps 14, respectively, by means of hot melt adhesives (not shown) so that, upon being relieved of tension, these elastic members may be free to contract and thereby to form the respective flaps with gathers.

The chassis 1 further includes a pair of barrier cuffs 17 extending in parallel to each other in a longitudinal direction of the chassis 1. The respective barrier cuffs 17 have proximal edges 17a joined to upper surfaces of the respective side flaps 13 in the vicinity of the side edges of the core 11 by means of hot melt adhesives or a welding means (not shown). Distal segments 17b of the barrier cuffs 17 which are contiguous to the proximal edges 17a are elasticized in a longitudinal direction thereof. Each of these distal segments 17b is elasticized by at least one elastic member 18 attached in a stretched state to the cuff 17 along its distal edge 17c.

As has already been described, the chassis 1 still further includes the pair of stretchable ear flaps 19. These ear flaps 19 respectively have proximal ends 19a joined to transversely opposite lateral zones of the rear waist regions 4 by means of hot meld adhesives or a welding means (not shown) and distal segments 19b which are contiguous to the proximal ends 19a. A part of the rear waist region 4 defined between the ear flaps 19 is elastically stretched as these ear flaps 19 are pulled outward against a contractile force thereof. In this way, such a part of the rear waist region 4 is brought in close contact with the diaper-wearer's skin when the diaper is worn.

Figure 3:
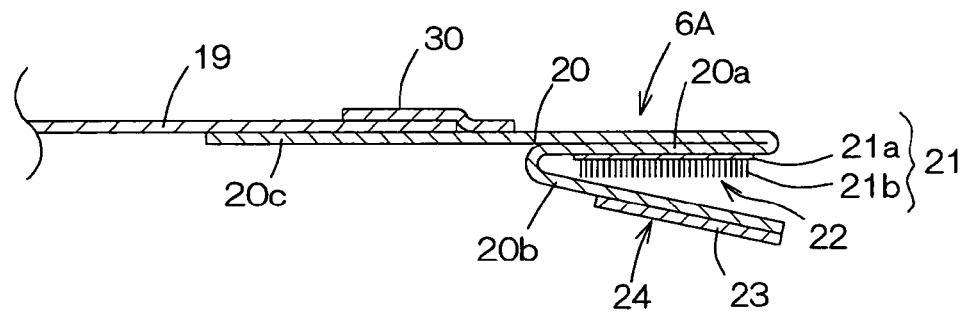
FIG. 3 is a sectional view taken along the line 3-3 in FIG. 1.

Referring to FIG. 3, each of the engaging fasteners 6A includes a backing 20 in the form of an elongate, a stiff panel 20 folded to define backing segments 20a, 20b wherein the backing segment 20b slants at a given angle, preferably at the angle in a range of 3° to 30° with respect to the backing segment 20a. The backing segment 20b can be pressed into contact with the backing segment 20a but elastically detached therefrom as the backing segment 20b is relieved of such a pressing force. The engaging fastener 6A may be secured to the associated ear flap 19 by pinching the ear flap 19 between a backing segment 20c and a protector 30, followed by assembling them together using suitable adhesives or a welding means (not shown) Stapling or riveting also may be used to assemble them together.

A hook member 21 having a plurality of hook elements 21b projecting from a backing 21a may be secured to the backing segment 20a forming a part of the engaging fastener 6A by means of suitable adhesives (not shown) and thereby an engaging means 22 may be formed. To the backing segment 20b forming the other part of the engaging fastener 6A, in turn, a smooth sheet member 23 having a ground color different from that of the backing segment 20b and serving as a shape retaining means may be integrally joined by means of suitable adhesives (not shown) and thereby an insert 24 may be formed.

Figure 4:
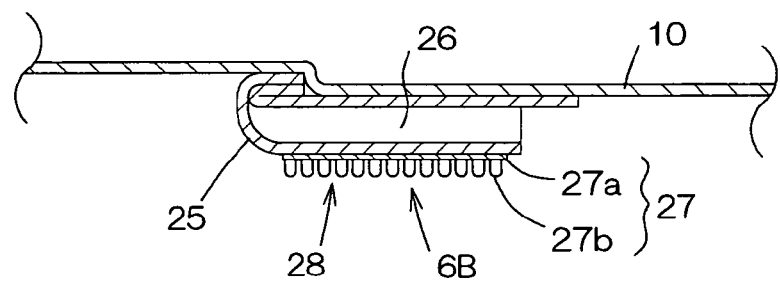
FIG. 4 is a sectional view taken along the line 4-4 in FIG. 1.

Referring now to FIG. 4, each of the landing fasteners 6B is formed by a sleeve 25 and a pocket 26. The pocket 26 opens outward with respect to the associated side edge of the front waist region 3. The sleeve 25 is formed from a flexible sheet and secured to the outer sheet 10 facing the wearer's garment in the front waist region 3 by means of suitable adhesives or a welding means (not shown). A loop member 27 having a plurality of loop elements 27b projecting from a backing segment 27a is secured to an upper surface of the sleeve 25 by means of suitable adhesives (not shown). Assumed that the sleeve 25 comprises a fibrous or reticular webwork, the loop elements 27b can be formed utilizing such a webwork itself. In this manner, the sleeve 25 is formed on its upper surface with landing means 28 with which the engaging means 22 can be releasably engaged.

Figure 5:
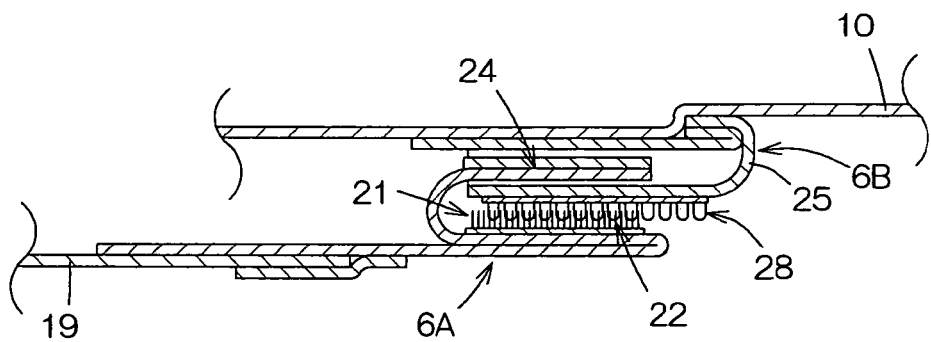
FIG. 5 is a sectional view taken along the line 5-5 in FIG. 1.

When it is desired to connect the front and rear waist regions 3, 4 with each other, as illustrated in details in FIG. 5, the insert 24 of the engaging fastener 6A may be introduced into the pocket 26 of the landing fastener 6B through the opening of the pocket 26 and then the engaging means 22 of the engaging fastener 6A may be pressed against the landing means 28 so as to engage the latter. In order to ensure that the insert 24 can be smoothly introduced into the pocket 26, the insert 24 preferably has a stiffness value in a range of 0.05N/cm to 2N/cm as measured by the Taber's method.

While not illustrated in details, the hook member 21 constituting the engaging means 22 may be replaced by a pressure-sensitive adhesive. In this case, the pressure-sensitive adhesive is protectively covered with a release paper. It is also possible that the engaging means 22 is formed on its outer end with a finger-grip tab.

The inner sheet 9, the outer sheet 10 and the core 11 may be formed using materials commonly used for disposable diapers of prior art. Particularly, the inner sheet 9 may be formed from a fibrous nonwoven fabric, a porous plastic film or the like, the outer sheet 10 may be formed from a moisture-pervious plastic film or a laminate of such a film and a fibrous nonwoven fabric and the core 11 may be formed from a mixture of fluff pulp and super-absorbent polymer particles or the like.

The elastic members 15, 16, 18 also may be formed from materials commonly used for disposable diapers of prior art, for example, a natural rubber, a synthetic rubber, an urethane foam or the like.

The ear flap 19 may be formed using a stretchable nonwoven fabric of prior art. While it has previously been described that the elastically stretchable zone of the waist region is defined between a pair of the ear flaps 19, it is possible to replace the ear flaps 19 by a stretchable nonwoven fabric forming this zone having a desired width dimension and provided with a plurality of thread-like elastic members spaced one from another.

What is claimed is:

1. A wearing article, comprising:
   first and second waist regions each having a body-facing surface and a garment-facing surface, said first and second waist regions cooperating together to define a waist-opening, a crotch region extending between and cooperating with said first and second waist regions to define a pair of leg-openings, and a fastening system releasably connecting said first and second waist regions;
   said fastening system comprising engaging fasteners respectively located on transversely opposite side edges of said first waist region and landing fasteners located on said garment-facing surface of transversely opposite side zones of said second waist region, wherein each of said engaging fasteners has an insert and an engaging portion while each of said landing fasteners has a pocket adapted to receive said insert and a landing portion formed on an outer surface of said pocket so that said engaging portion releasably engages said landing portion; and
   at least one of said first and second waist regions being provided with elastic members serving to elastically adjust a circumferential waist dimension defined by said first and second waist regions;
   wherein, when the engaging portion releasably engages the landing portion, the insert is received in the pocket, without positively and directly engaging an inner surface of the pocket;
   wherein the insert, if pressed into contact with the engaging portion by a pressing force, is elastically detached from said engaging portion when the insert is relieved of the pressing force;
   wherein each of said engaging portions comprises a hook member having a plurality of hooks projecting from a backing of said hook member towards said insert;
   wherein each of said pockets has an opening oriented towards an adjacent side edge of said second waist region; and
   wherein each of said landing portions comprises a fibrous web defining the outer surface of said pocket, said fibrous web being releasably engageable with the hooks of the corresponding engaging portion when the corresponding engaging portion releasably engages said landing portion.

2. The wearing article as defined by claim 1, wherein said engaging fasteners and said landing fasteners are located along an elastically stretchable and contractible line created by said elastic members on said first and second waist regions.

3. The wearing article as defined by claim 1, wherein, in each of said engaging fasteners, said insert slants at an acute angle with respect to said engaging portion when the engaging portion is not engaged with the corresponding landing portion 4. A wearing article, comprising:
   first and second waist regions each having a body-facing surface and a garment-facing surface, said first and second waist regions cooperating together to define a waist-opening, a crotch region extending between and cooperating with said first and second waist regions to define a pair of leg-openings, and a fastening system releasably connecting said first and second waist regions;
   said fastening system comprising engaging fasteners respectively located on transversely opposite side edges of said first waist region and landing fasteners located on said garment-facing surface of transversely opposite side zones of said second waist region, wherein each of said engaging fasteners has an insert and an engaging portion while each of said landing fasteners has a pocket adapted to receive said insert and a landing portion formed on an outer surface of said pocket so that said engaging portion releasably engages said landing portion; and
   at least one of said first and second waist regions being provided with elastic members serving to elastically adjust a circumferential waist dimension defined by said first and second waist regions;
   wherein, when the engaging portion releasably engages the landing portion, the insert is received in the pocket, without positively and directly engaging an inner surface of the pocket;
   wherein the insert, if pressed into contact with the engaging portion by a pressing force, is elastically detached from said engaging portion when the insert is relieved of the pressing force;
   wherein each of said engaging portions comprises a hook member having a plurality of hooks projecting from a backing of said hook member towards said insert;
   wherein each of said pockets has an opening oriented towards an adjacent side edge of said second waist region; and
   wherein each of said landing portions comprises a loop member having a plurality of loops projecting from a sheet secured to the outer surface of said pocket, said loops being releasably directly engageable with the hooks of the corresponding engaging portion when the corresponding engaging portion releasably engages said landing portion.

5. The wearing article as defined by claim 1, wherein said first waist region comprises a pair of elastically stretchable and contractible ear flaps on the side edges thereof, and said engaging fasteners are attached to outer side edges of said ear flaps, respectively.

6. The wearing article as defined by claim 1, wherein said first and second waist regions and said crotch region are formed by an absorbent chassis comprising, in turn, a liquid-pervious inner sheet, a liquid-impervious outer sheet and a liquid-absorbent core interposed between said inner and outer sheets.

7. A wearing article, comprising:
   first and second waist regions and a crotch region extending between said waist regions; and
   a fastening system for releasably connecting said waist regions;
   said fastening system comprising:
      a pair of engaging fasteners respectively attached to transversely opposite sides of said first waist region, each of said engaging fasteners having an insert and an engaging portion which is not positioned on said insert; and a pair of landing fasteners respectively attached to transversely opposite sides of said second waist region, each of said landing fasteners having a pocket and a landing portion which is not positioned in said pocket;

wherein each of said engaging fasteners and the corresponding one of said landing fasteners have an engaged state in which the engaging portion of said engaging fastener releasably directly engages the landing portion of the corresponding landing fastener and the insert of said engaging fastener is received, without positively and directly engaging, the pocket of the corresponding landing fastener; and a disengaged state in which the engaging portion of said engaging fastener disengages from the landing portion of the corresponding landing fastener and the insert of said engaging fastener is entirely located outside the pocket of the corresponding landing fastener;

wherein each of said engaging portions comprises a hook member having a plurality of hooks projecting from a backing of said hook member towards said insert;

wherein each of said pockets has an opening oriented towards an adjacent side edge of said second waist region; and wherein each of said landing portions comprises a fibrous web on an outer surface of said pocket, said fibrous web being directly releasably engaged with the hooks of the corresponding engaging portion in the engaged state.

8. The wearing article of claim 7, wherein, in said engaged state, the landing portion of said landing fastener is sandwiched between the insert and the engaging portion of the engaging fastener.

9. The wearing article as defined by claim 8, wherein the opening of each of said pockets, through which the insert of the corresponding engaging fastener is introduced into said pocket, is oriented away from the other pocket.

10. The wearing article as defined by claim 8, wherein said first waist region comprises a pair of elastically stretchable and contractible wing flaps on the transversely opposite sides thereof, and said engaging fasteners are respectively attached to outer side edges of said wing flaps.

11. A wearing article, comprising:
front and rear waist regions and a crotch region longitudinally extending between said waist regions; and
a fastening system for releasably connecting said waist regions, said fastening system comprising a pair of first fastening elements respectively located on transversely opposite sides of said front waist region, and a pair of second fastening elements respectively located on transversely opposite sides of the rear waist region;
wherein each of said first fastening elements comprises:
a proximal portion attached to said front waist region;
a distal portion spaced from an outer surface of said front waist region and having opposite inner and outer surfaces facing towards and away from the outer surface of said front waist region, respectively, wherein a space between the inner surface of said distal portion and the outer surface of said front waist region defines a pocket; and
a landing zone on the outer surface of said distal portion;
wherein each of said second fastening elements comprises:
a main portion having a distal end and a proximal end, the proximal end being attached to a corresponding one of the transversely opposite sides of said rear waist region, the distal end extending transversely outwardly beyond said corresponding one of the transversely opposite sides of said rear waist region, said main portion further comprising opposite inner and outer surfaces;
an engaging member on the inner surface and at the distal end of said main portion, said engaging member being releasably engageable with the landing zone of the corresponding first fastening element; and
a branch portion connected to the inner surface of said main portion at a location between said proximal and distal ends of said main portion, wherein when the corresponding engaging member and landing zone are engaged, said branch portion is receivable in the pocket of the corresponding first fastening element and is contactable with, without positively and directly engaging, the inner surface of said distal portion and the outer surface of said front waist region that define therebetween said pocket;
wherein each of said engaging members comprises a hook member having a plurality of hooks projecting from a backing on the inner surface of the distal end of said main portion towards said branch portion;
wherein each of said pockets has an opening oriented towards an adjacent side edge of said front waist region; and
wherein each of said landing zones is defined by a fibrous web on the outer surface of said distal portion, said fibrous web being releasably directly engaged with the hooks of the corresponding engaging member when the corresponding engaging member and landing zone are engaged.

12. The wearing article of claim 11, wherein, when the corresponding engaging member and landing zone are engaged,
the distal portion of said first fastening element is sandwiched between (i) the branch portion and (ii) the hooks on the distal end of the main portion of the second fastening element; and
the branch portion of the second fastening element is sandwiched between the distal portion of said first fastening element and the front waist region.

13. The wearing article as defined by claim 11, wherein said rear waist region comprises a pair of elastically stretchable and contractible wing flaps on the transversely opposite sides thereof, and the proximal ends of the main portions of the second fastening elements are respectively attached to said wing flaps.

14. The wearing article as defined by claim 11, wherein, in each of said second fastening elements, the branch portion extends away from the proximal ends of the main portion and defines, together with the distal end of the main portion, an acute angle when the corresponding engaging member and landing zone are not engaged.

15. The wearing article as defined by claim 11, wherein each of said second fastening elements comprises a backing sheet defining both said main portion and said branch portion, said backing sheet comprising:
a fixed end attached to the rear waist region and defining the proximal end of the main portion;
first and second folds in which said backing sheet is folded in opposite directions, said distal end of the main portion being defined by multiple layers of said backing sheet between said first fold and said second fold; and
a free end, said branch portion being defined between the second fold and said free end.

16. The wearing article as defined by claim 11, wherein each of said second fastening elements further comprises a shape retaining sheet attached to said branch portion, said shape retaining sheet having an exposed smooth surface for facilitating introduction of said branch portion into the pocket of the corresponding first fastening element, said exposed smooth surface facing the outer surface of said front waist region when the branch portion is received in the pocket of the corresponding first fastening element.

17. The wearing article as defined by claim 11, wherein, when the branch portion is not received in the corresponding pocket, the branch portion is normally free of direct contact with the hooks of the engaging member, and the branch portion, if pressed into direct contact with the hooks of the engaging member by a pressing force, is elastically detached from the direct contact with said hooks when the branch portion is relieved of the pressing force.

18. The wearing article as defined by claim 7, wherein the insert, if pressed into direct contact with the engaging portion by a pressing force, is elastically detached from direct contact with said engaging portion when the insert is relieved of the pressing force.

* * * * *